(12) United States Patent
Martynus et al.

(10) Patent No.: US 9,050,218 B2
(45) Date of Patent: Jun. 9, 2015

(54) DIAPER WITH SEPARATOR SHEET

(71) Applicant: The Procter & Gamble Company, Cincinnati, OH (US)

(72) Inventors: Cornelia Beate Martynus, Nidderau-Osteim (DE); Rolf Hecker, Kriftel (DE); Sandra Freiboth, Leiderbach (DE); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/171,060

(22) Filed: Feb. 3, 2014

(65) Prior Publication Data

US 2014/0221956 A1 Aug. 7, 2014

Related U.S. Application Data

(60) Provisional application No. 61/759,483, filed on Feb. 1, 2013.

(51) Int. Cl.
| | |
|---|---|
| *A61F 13/15* | (2006.01) |
| *A61F 13/20* | (2006.01) |
| *A61F 13/49* | (2006.01) |
| *A61F 13/56* | (2006.01) |
| *A61F 13/494* | (2006.01) |
| *A61F 13/495* | (2006.01) |

(52) U.S. Cl.
CPC ....... *A61F 13/49017* (2013.01); *A61F 13/5638* (2013.01); *A61F 13/49406* (2013.01); *A61F 13/49413* (2013.01); *A61F 13/495* (2013.01); *A61F 2013/4951* (2013.01); *A61F 2013/4956* (2013.01)

(58) Field of Classification Search
CPC ............ A61F 13/49017; A61F 13/495; A61F 2013/4956; A61F 13/49413; A61F 2013/4951; A61F 13/49019; A61F 13/494; A61F 13/49406; A61F 13/49446; A61F 2013/49022; A61F 2013/4948
USPC .......................... 604/385.01, 385.19, 385.28
See application file for complete search history.

(56) References Cited

U.S. PATENT DOCUMENTS

| | | | |
|---|---|---|---|
| 6,010,490 A | 1/2000 | Freeland et al. | |
| 6,152,907 A | 11/2000 | Widlund et al. | |
| 6,152,908 A | 11/2000 | Widlund et al. | |
| 6,824,534 B2 | 11/2004 | Mishima et al. | |
| 6,843,134 B2 | 1/2005 | Anderson et al. | |
| 7,062,983 B2 | 6/2006 | Anderson et al. | |
| 7,563,257 B2 | 7/2009 | Nakajima et al. | |
| 7,918,838 B2 | 4/2011 | Minato et al. | |
| 8,168,853 B2 | 5/2012 | Autran et al. | |
| 8,197,457 B2 | 6/2012 | Suzuki et al. | |
| 2006/0009746 A1* | 1/2006 | Nakajima et al. | 604/385.19 |
| 2007/0156110 A1 | 7/2007 | Thyfault | |
| 2011/0060307 A1* | 3/2011 | Nakajima et al. | 604/385.25 |

OTHER PUBLICATIONS

PCT International Search Report mailed Apr. 9, 2014 (9 pages).

* cited by examiner

*Primary Examiner* — Melanie Hand
*Assistant Examiner* — Aundria Hairell
(74) *Attorney, Agent, or Firm* — William E. Gallagher

(57) ABSTRACT

Diapers, including infant diapers, training pants, and adult incontinence articles, and the like having a transverse separator sheet for excrement separation and/or isolation away from the skin with a specific design of attachment of the transverse separator sheet to the topsheet and to the elastic cuffs of the diapers.

14 Claims, 6 Drawing Sheets

DIAPER WITH SEPARATOR SHEET

FIELD OF THE INVENTION

This invention is directed to diapers, including infant diapers, including training pants, and adult incontinence articles, and the like having a specific transverse separator sheet for excrement separation and/or isolation away from the skin

BACKGROUND OF THE INVENTION

Several diaper types have been proposed with components to reduce leakage of feces and urine from the diaper, to reduce soiling of the genitals or other skin by the feces, or to reduce mixing of urine and feces, to further reduce the risk of irritation of the skin. For example, diapers with a topsheet with an opening, providing a passageway to a void space for collected feces and urine have been proposed; also proposed are diapers with two openings to receive the urine and feces in separate areas; also proposed are diapers with a transversely positioned three-dimensional resilient barrier wall or partition placed in the centre of the diaper, to receive feces and urine respectively on either side of said wall or partition, and to avoid migration of the feces to the front of the article, beyond the separator, or combinations of the above solutions. An example of such a topsheet structure with longitudinal elasticated portions and a transverse portion with a partition is described in for example U.S. Pat. No. 7,918,838; however, such large structures may add significant cost to the product. Furthermore, if the central partition portion is too large, there is a risk that, upon misplacement of the diaper, feces or urine is received on this portion.

Simpler transversely positioned partitions are for example described in EP 674499, which describes a transverse separator sheet attached to the longitudinal cuffs and to the topsheet of a diaper. The inventors found however that the design of the attachments areas to both the cuffs and the topsheet of such a transverse separator sheet may have a negative impact on the comfort, fit and absorbency properties of diapers comprising such a transverse separator sheet.

Therefore, the present invention provides a diaper with a specific design for both the cuff attachment areas and the topsheet attachment area(s) which has a limited impact on the comfort, fit and absorbency properties of the diaper.

SUMMARY OF THE INVENTION

The invention relates to an infant or adult diaper having a longitudinal centerline and a lateral centerline perpendicular to the longitudinal centerline. The diaper comprises a topsheet and a backsheet and positioned therein between an absorbent core, and a first and second longitudinally extending opposing elastic cuffs, positioned on either longitudinal side of the topsheet. The diaper has a crotch region, positioned in between a front region and a back region. The diaper comprises a transverse separator sheet made of a separator sheet material. The transverse separator sheet has a transversely extending top edge and top edge portion and an opposing transversely extending bottom edge and bottom edge portion. Parts of the top edge portion are attached to the cuffs in the crotch region or front region of the diaper thereof by means of attaching a first attachment area of the top edge portion to the first cuff in the crotch region or front region of the diaper and a second opposing attachment area of the top edge portion to the second cuff in the crotch region or front region of the diaper, to form a first cuff attachment area and a second cuff attachment area. Each cuff attachment area has an inner edge towards the longitudinal centerline of the diaper. Part(s) or all of the bottom edge portion are attached to the topsheet with one or more topsheet attachment area(s). The first cuff attachment area has a first projected bond length as measured according to the projected bond measurement test method and the second cuff attachment area has a second projected bond length as measured according to the projected bond measurement test method. The average of the first and second projected bond lengths is from 1% to 20% or from 2% to 15% of the longitudinal dimension of the crotch region (B) of the diaper (1).

DETAILED DESCRIPTION OF THE INVENTION

Figure 1:
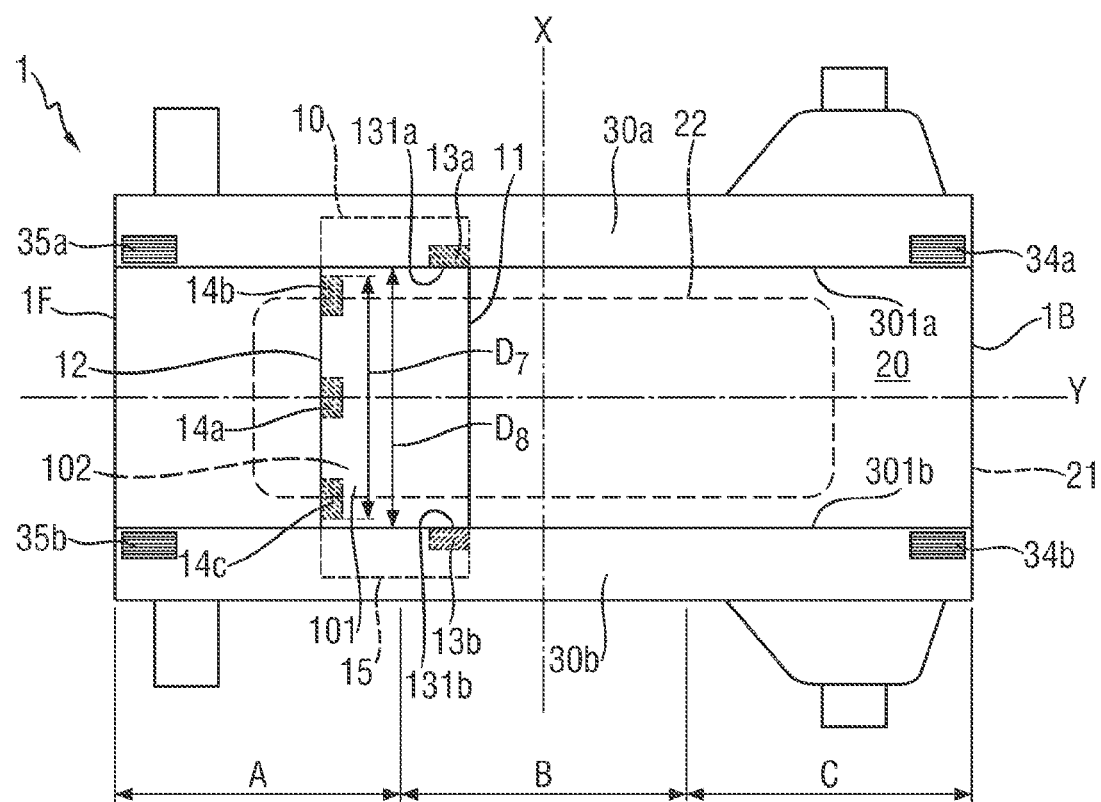
FIG. 1 shows a top view of a diaper according to an embodiment of the present invention in flat state.
Figure 2:
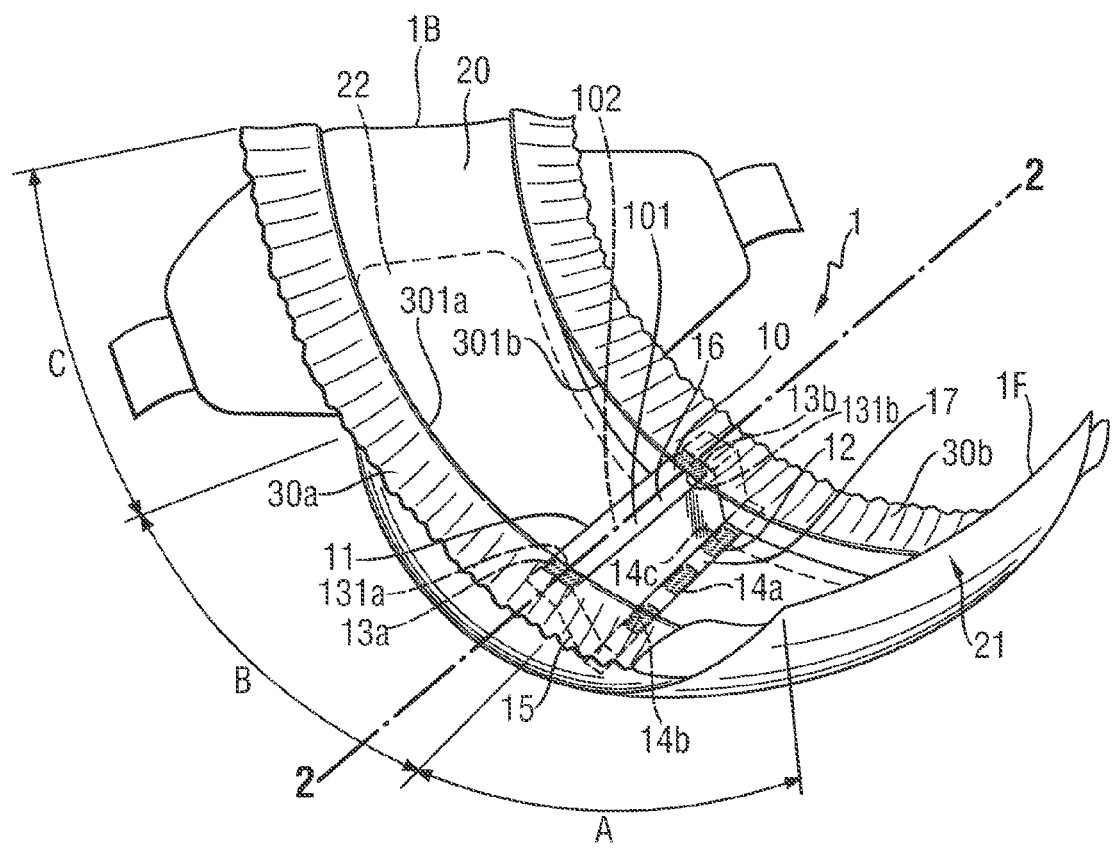
FIG. 2 shows a perspective view of the diaper of FIG. 1.

"Diaper" is used herein, to refer to absorbent articles to be placed about the wearer's lower torso, and include infant (baby and toddler) diapers and adult diapers, and it includes so-called diapers with fasteners, to be fastened around the lower torso, and pant-type diapers.

"Front region" (A) and 'back region' (C) are used herein to refer to the two regions of the diaper, which are in use, respectively, the closest to the front of the wearer and the back of the wearer, each spanning the transverse dimension of the diaper, and each having a longitudinal dimension that is one third of the longitudinal dimension of the diaper.

"Crotch region" is used herein to refer to the region of the diaper which is positioned between the front region and the back region, having also a longitudinal dimension that is one third of the longitudinal dimension of the diaper.

For embodiments, wherein the front edge and/or back edge of the diaper is/are not configured as a straight line extending parallel to the transverse centerline (X) of the diaper, the longitudinal dimension of the diaper corresponds to the longitudinal dimension measured between the transverse line extending parallel to the transverse centerline (X) of the diaper and passing through the point of the front edge of the diaper which is closest to the transverse centerline (X) of the diaper and the transverse line extending parallel to the transverse centerline (X) of the diaper and passing through the point of the back edge of the diaper which is closest to the transverse centerline (X) of the diaper. For such embodiments, the longitudinal dimension of the front region or the back region is measured starting from respectively the transverse line extending parallel to the transverse centerline (X)

of the diaper and passing through the point of the front edge of the diaper which is closest to the transverse centerline (X) of the diaper or the transverse line extending parallel to the transverse centerline (X) of the diaper and passing through the point of the back edge of the diaper which is closest to the transverse centerline (X) of the diaper.

"Longitudinal" is used herein to refer to the direction which is running substantially parallel or exactly parallel to the longitudinal centerline (Y) of the diaper or topsheet, which may be the machine direction (MD) of the process.

"Lateral" or "transverse" is used herein to refer to the direction which is substantially perpendicular or exactly perpendicular to the longitudinal centerline (Y) of the diaper or topsheet, which may be the cross-machine direction of the process (CD).

"Z-direction" is used herein to refer to the direction perpendicular to the longitudinal direction and perpendicular to the transverse or lateral direction.

"Longitudinal dimension", "transverse dimension" or "Z-dimension" is used herein to refer to the dimension of the diaper or element thereof, e.g. elastic cuff or topsheet or transverse separator sheet or transverse separator sheet material or region of the diaper, which is measured respectively in the longitudinal direction, transverse direction or Z-direction of the diaper or element thereof, e.g. elastic cuff or topsheet or transverse separator sheet or transverse separator sheet material or region of the diaper.

"Substantially perpendicular" or "substantially parallel" is used herein to refer to directions within 30° or 20° or 10° or 5° from the exact perpendicular or parallel direction, unless stated or specified otherwise.

As used herein, "along" means 'at least partially substantially parallel to and adjacent to'.

"Top edge" or "top edge portion" is used herein to refer to respectively the transversely extending edge or transversely extending edge portion of the separator sheet 10 or separator sheet material which is in contact with the wearer's body when the diaper 1 is applied to a wearer.

"Bottom edge" or "bottom edge portion" is used herein to refer to respectively the transversely extending edge or transversely extending edge portion of the separator sheet 10 or separator sheet material 15 which is more remote from the wearer's body (compared to the top edge or top edge portion) when the diaper 1 is applied to a wearer.

"Relaxed" or "relaxed state" or "contracted" or "contracted state" is used herein to refer to the state of the diaper or separator sheet or separator sheet material wherein no forces are applied to respectively the diaper or separator sheet or separator sheet material.

"Flat state" is used herein to refer to the state of the diaper when the diaper is laid out flat onto an even horizontal surface.

"Distal edge" is used herein to refer to the longitudinally extending edge of an elastic cuff which in use is closer to the wearer's body than the other longitudinally extending edge of the same elastic cuff.

"Maximum transverse dimension of the one or more topsheet attachment area(s)" is used herein to refer to the transverse dimension of the topsheet attachment area(s) which is measured between the two points of the topsheet attachment area(s) which are the most distant from each other including gaps between two attachment areas in case there is more than one topsheet attachment area, in flat state of the diaper 1.

"Minimum transverse dimension between the longitudinally extending distal edges of the first and second elastic cuffs" is used herein to refer to the minimum transverse dimension which is measured between the longitudinally extending distal edges of the first and second elastic cuffs, in flat state of the diaper with the first and second cuff attachment areas being detached from the first and second elastic cuffs.

"Strain" is used herein to refer to the engineering strain which is defined hereinafter in the test methods section of this application.

"Apertured topsheet" is used herein to refer to a topsheet which comprises at least one effective aperture.

"Effective aperture" is used herein to refer to any hole through a topsheet having a gray level less than or equal to 18 on a standard grey level scale of 0-255 under image acquisition parameters described in the topsheet effective aperture size and percentage open area measurement test method.

"Effective aperture pattern density" is used herein to refer the percentage of the surface area of an apertured topsheet which is covered with effective apertures.

"Bonding pattern density" is used herein to refer to the percentage of the surface area of a cuff attachment area or a topsheet attachment area which is covered with the one or more individual bond(s) which are comprised by the cuff attachment area or the topsheet attachment area.

The diaper 1 according to the present invention has a longitudinal centerline Y and a lateral centerline X perpendicular to the longitudinal centerline Y. The diaper 1 comprises a topsheet 20, a backsheet 21 and positioned therein between an absorbent core 22. The diaper 1 further comprises a pair of longitudinally extending opposing elastic cuffs 30a, 30b positioned on either longitudinal side of the topsheet 20. The diaper 1 has a crotch region B positioned in between a front region A and a back region C.

The diaper 1 comprises a transverse separator sheet 10 made of a separator sheet material 15 as for example shown in FIGS. 1 to 8.

Transverse Separator Sheet

The transverse separator sheet 10 herein is an individual sheet that is attached to a pair of opposing elastic cuffs 30a, 30b and to a topsheet 20. The separator sheet 10 prior to attachment to the cuffs 30a, 30b or topsheet 20 is herein referred to as separator sheet material 15. The separator sheet material 15 may be cut from a separator sheet material web.

The separator sheet 10 may be present in the front region A and/or crotch region B of the diaper 1; if present in the front region A of the diaper 1, it is in close proximity to the crotch region B, in the back half of the front region A of the diaper 1. For example, the minimum distance between the topsheet attachment area(s) 14 and the front edge 1F of the topsheet 20 or diaper 1 may be from 20%, or 25%, or 30% to 60%, or to 50% or to 40% of the average longitudinal dimension (average length) of the topsheet 20 or diaper 1, respectively.

The separator sheet 10 and separator sheet material 15 have first and second transversely extending, opposing, edges and edge portions, herein referred to as a top edge 11 and top edge portion 16, and as a bottom edge 12 and bottom edge portion 17. The top edge 11 and bottom edge 12 are connected to one another by two opposing side edges of the separator sheet 10 or separator sheet material 15. It should be understood that the two opposing side edges of the separator sheet material 15 which connect the top edge 11 to the bottom edge 12 of the separator sheet material 15 may be substantially perpendicular to the top edge 11 of the separator sheet material, when the separator sheet material 15 is laid out flat in relaxed, contracted state onto an even horizontal surface. It should also be understood that some portions of the two opposing side edges of the separator sheet 10 which connect the top edge 11 to the bottom edge 12 of the separator sheet 10 may have in use a Z-direction orientation.

The separator sheet material 15 may have when laid out flat onto an even horizontal surface in relaxed, contracted state, a longitudinal dimension (length), also referred to as the separator sheet's longitudinal dimension (length) in relaxed state of the separator sheet 10 and the separator sheet material 15 may have when laid out flat onto an even horizontal surface in relaxed, contracted state, a transverse dimension (width), also referred to as the separator sheet's transverse dimension (width) in relaxed state of the separator sheet 10. It should be understood that the width of the separator sheet 10 or separator sheet material 15 may be longer than the length of respectively the separator sheet 10 or separator sheet material 15.

The separator sheet 10 may have a minimum longitudinal dimension in relaxed state of the separator sheet 10 between the top edge 11 and the bottom edge 12 of the separator sheet 10 of from 3.0 cm, or from 4.0 cm, or from 5.0 cm, to for example 15.0 cm or to 10.0 cm or to 8.0 cm or to 7.0 cm, or to 6.0 cm or to 5.1 cm.

The separator sheet 10 may have an average transverse dimension in relaxed state of the separator sheet 10 of at least 2.5 cm, or at least 4.0 cm, or at least 5.0 cm to less than 12.0 cm or less than 10.0 cm.

Attachment of the Separator Sheet to the Elastic Cuffs

Parts of the top edge portion 16 of the separator sheet 10 are attached to the elastic cuffs 30a, 30b in the crotch region B or front region A of the diaper 1 thereof. A first cuff attachment area 13a and a second cuff attachment area 13b are formed by attaching respectively a first attachment area of the top edge portion 16 to the first cuff 30a in the crotch region B or front region A of the diaper 1 and a second opposing attachment area of the top edge portion 16 to the second cuff 30b in the crotch region B or front region A of the diaper 1. Each of the first and second cuff attachment areas 13a, 13b has an inner attachment area edge 131a, 131b which is the edge of attachment area 13a, 13b which is the closest to the longitudinal centerline Y of the topsheet 20 or diaper 1. Thus, there is a (central) part of the top edge portion 16 which is not attached to either of the cuffs 30a, 30b. The minimum transverse dimension of this (central) part of the separator sheet 10 in relaxed, contracted state of the separator sheet 10, i.e. the separator sheet's minimum transverse dimension of the separator sheet 10 in relaxed state of the separator sheet 10 measured between the opposing inner attachment area edges 131a, 131b may be at least 20 mm, or at least 30 mm. It may be up to 60 mm, or up to 55 mm or up to 50 mm or up to 45 mm.

The first cuff attachment area 13a has a first projected bond length $D_{4a}$, as measured according to the projected bond measurement test method and the second cuff attachment area 13b has a second projected bong length $D_{4b}$, as measured according to the projected bond measurement test method. The average of the first and second projected bond length $D_{4a}$, $D_{4b}$ may be from 1% to 20% or from 2% to 15% of the longitudinal dimension of the crotch region (B) of the diaper (1). The average of the first and second projected bond length $D_{4a}$, $D_{4b}$ may be from 3 mm to 25 mm or from 5 mm to 15 mm. This ensures that the top edge portion 16 which is in contact with the wearer's body is long enough to not create pressure marks on the wearer's skin when the diaper is applied to a wearer but not too long to avoid covering of the urination point and/or the anus point which would very likely reduce the absorbency properties of the diaper 1.

Each of the first and second elastic cuffs 30a, 30b has a longitudinally extending distal edge 301a, 301b. The minimum transverse dimension between the longitudinally extending distal edge of the first elastic cuff 301a and the inner attachment area edge of the first cuff attachment area 131a and/or the minimum transverse dimension between the longitudinally extending distal edge of the second elastic cuff 301b and the inner attachment area edge of the second cuff attachment area 131b is of 0 to 15 mm or 0 to 5 mm. Such a configuration is particularly advantageous in order to reduce the risk of migration of the feces above the transverse separator sheet 10 when the diaper 1 is loaded with bodily exudates.

The first and second cuff attachment areas 13a, 13b may be mirror images of one another in the longitudinal axis Y of the diaper 1, in flat state of the diaper 1 as for example shown in FIGS. 1 to 8.

The first and second cuff attachment areas 13a, 13b may have any shape. They may have a rectangular shape as shown for example in FIGS. 1 to 8. They may also have a round or an oval shape.

The inner edge(s) of the first and/or second cuff attachment area(s) 131a, 131b may be oriented parallel to the longitudinal centerline Y of the diaper 1 in flat state of the diaper 1, as for example shown in FIGS. 1, 2, 5 and 6.

The inner edge(s) of the first and/or second cuff attachment area(s) 131a, 131b may form an angle $\alpha_a$, $\alpha_b$ of more than 0° to less than 90° or of 15° to 70°, or 30° to 60°, or 40° to 50° with a longitudinal line parallel to the longitudinal centerline Y of the diaper 1, in flat state of the diaper 1 as for example shown in FIGS. 3, 4, 7 and 8. Such a configuration is particularly advantageous since it is possible to provide the transverse separator sheet 10 with a longer and therefore stronger cuff attachment area 13a, 13b without considerably increasing the projected bond lengths of the first and second cuff attachment areas $D4_a$, $D4_b$.

It should be understood that a non straight inner edge 131a, 131b is considered as being oriented parallel to the longitudinal centerline Y of the diaper 1 or as forming an angle $\alpha_a$, $\alpha_b$ of more than 0° with a longitudinal line parallel to the longitudinal centerline Y of the diaper 1 if the inner edge of the rectangle with the smallest area possible surrounding the cuff attachment area 13a, 13b is respectively oriented parallel to the longitudinal centerline Y of the diaper 1 or forming an angle $\alpha_a$, $\alpha_b$ of more than 0° with a longitudinal line parallel to the longitudinal centerline Y of the diaper 1, in flat state of the diaper 1. It should also be understood that a round shaped cuff attachment area 13a, 13b is considered as being parallel to the longitudinal centerline Y of the diaper 1, in flat state of the diaper 1.

Figure 3:
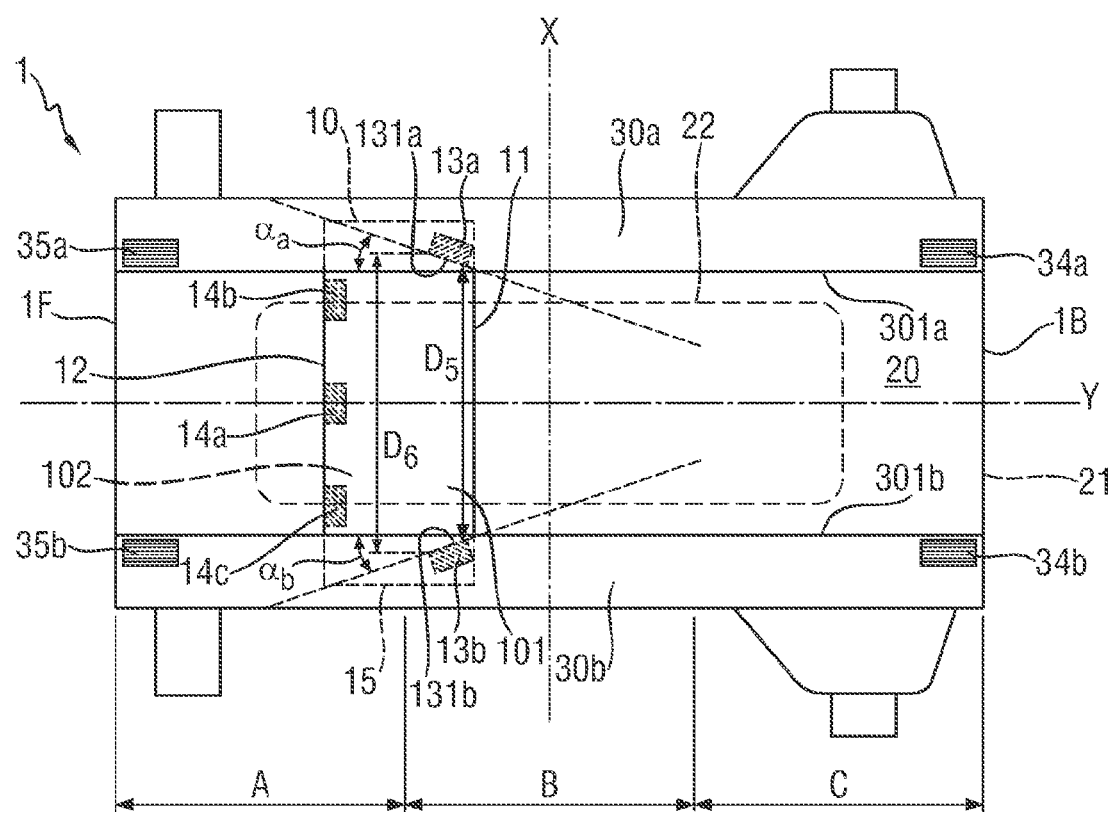
FIG. 3 shows a top view of a diaper according to another embodiment of the present invention in flat state.
Figure 4:
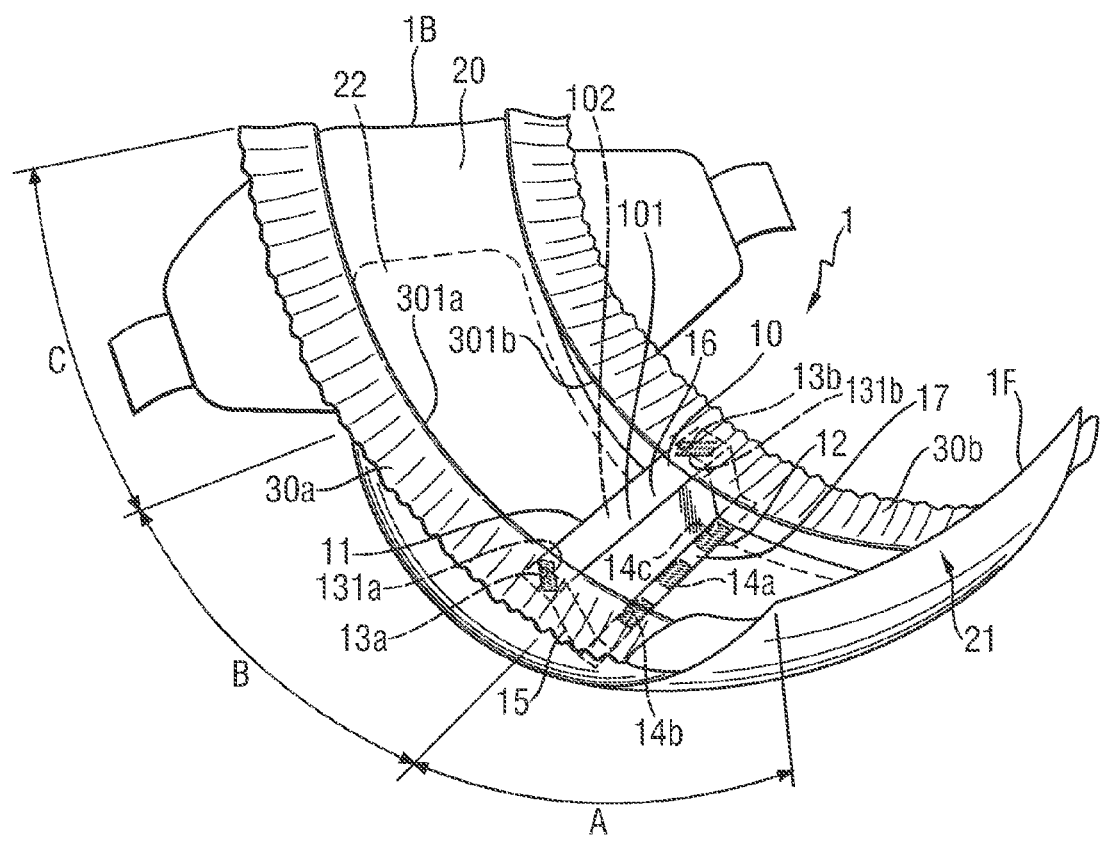
FIG. 4 shows a perspective view of the diaper of FIG. 3.
Figure 5:
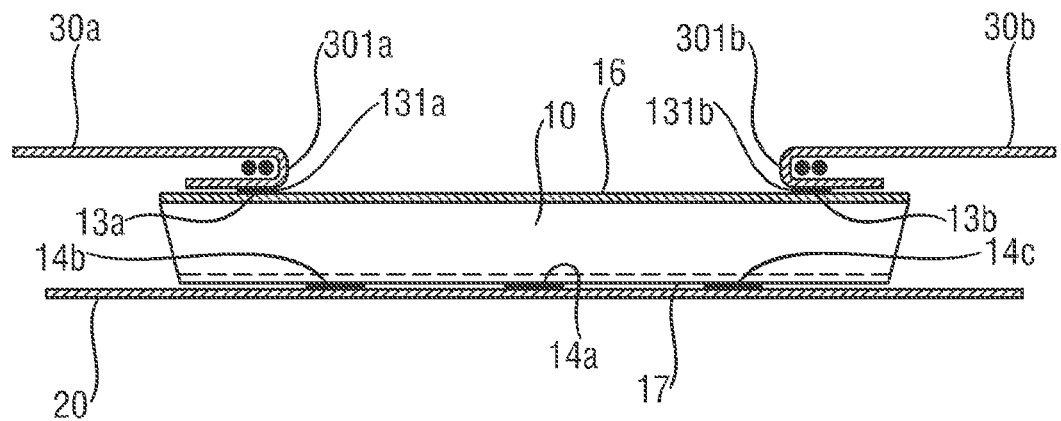
FIG. 5 shows a cross-sectional view of the diaper of FIG. 2 taken at the section tine 2-2.
Figure 6:
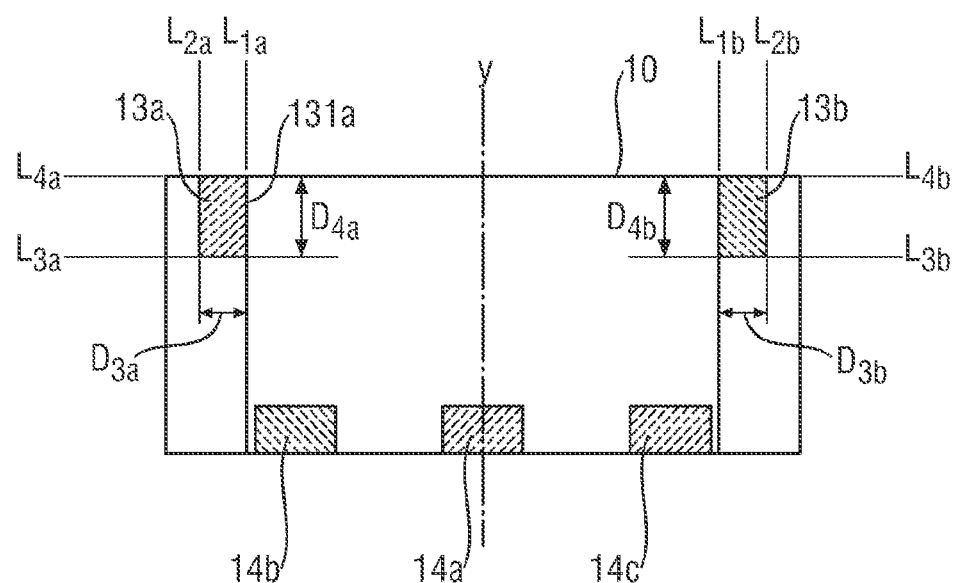
FIG. 6 shows a top view of the transverse separator sheet of FIG. 1 to illustrate how the projected bond lengths of cuff attachment areas is measured.
Figure 7:
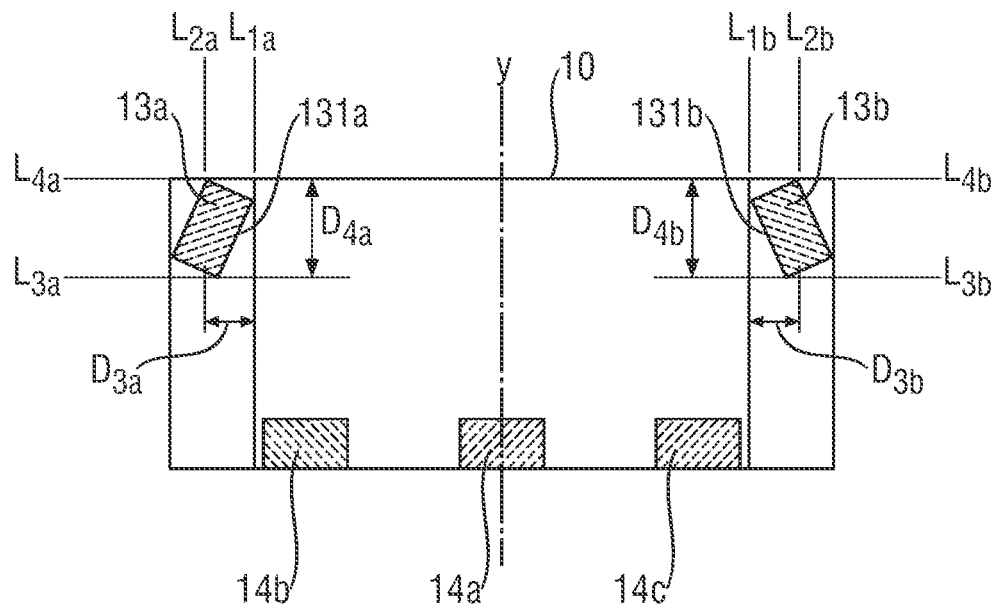
FIG. 7 shows a top view of the transverse separator sheet of FIG. 3 to illustrate how the projected bond lengths of a cuff attachment areas is measured.
Figure 8:
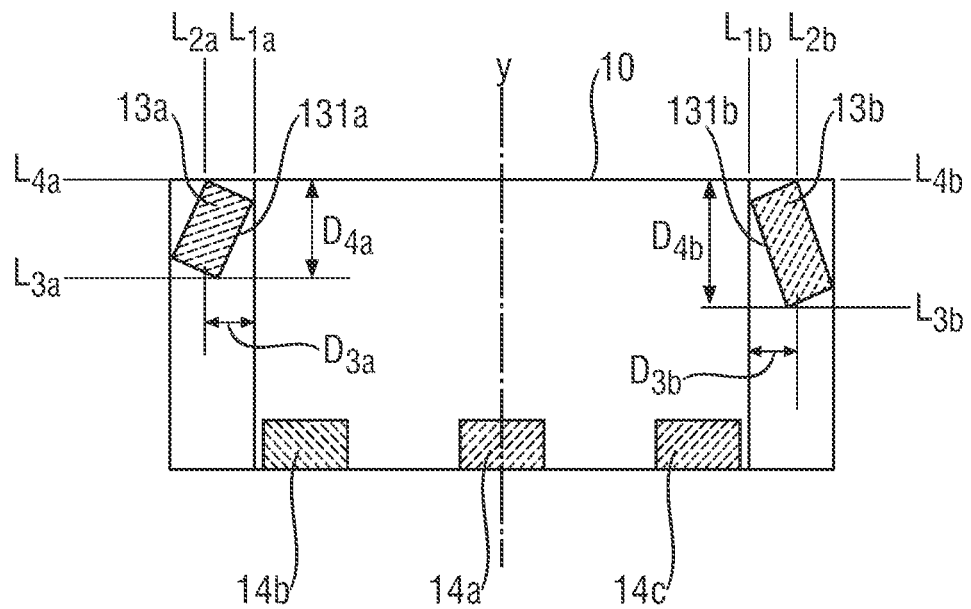
FIG. 8 shows a top view of a transverse separator sheet according to another embodiment of the present invention wherein the cuff attachment areas are not mirror images from one another in the longitudinal centerline of the diaper in fiat state of the diaper to illustrate how the projected bond lengths of cuff attachment areas is measured

One separator sheet's minimum transverse dimension $D_5$ in relaxed state of the separator sheet 10 between the opposing inner edges 131a, 131b of the first and second cuff attachment areas 13a, 13b may closer to the top edge 11 of the separator sheet 10 than one separator sheet's maximum transverse dimension $D_6$ in relaxed state of the separator sheet 10 between the opposing inner edges 131a, 131b of the first and second cuff attachment areas 13a, 13b as for example shown in FIG. 3.

Each cuff attachment area 13 may have an average transverse dimension of 3% to 40% or 5% to 35% or 5% to 25% of the average transverse dimension of the separator sheet 10.

The attachment of the separator sheet 10 to the elastic cuffs 30a, 30b can be done by adhesive bonding, pressure bonding, ultrasonic bonding or any other attachment mean known in the art. A cuff attachment area 13 may comprise one or more individual bond(s). Such individual bond(s) may be arranged according to a certain bonding pattern.

It should be understood that if a cuff attachment area 13 comprises more than one individual bond, these are herein considered as a single unitary cuff attachment area.

The bonding pattern density of the first and/or second cuff attachment area(s) 13a, 13b may be more than 20%, or more than 30%, or more than 40%, or more than 60%, up to 100%.

Attachment of the Separator Sheet to the Topsheet

Part(s) or all of the bottom edge portion 17 of the separator sheet 10 is/are attached to the topsheet 20 with one or more topsheet attachment area(s) 14. This may be in the front region A or crotch region B of the diaper 1 or topsheet 20.

Each of the one or more topsheet attachment area(s) 14 may have a maximum longitudinal dimension of from 1% to 10% or from 1% to 6% of the longitudinal dimension of the crotch region (B) of the diaper (1). Each of the one or more topsheet attachment area(s) 14 may have a maximum longitudinal dimension of from 1 mm to 15 mm or from 2 mm to 10 mm. This is particularly advantageous since it ensures that the bottom edge portion 17 of the separator sheet 10 is not too long and therefore does not cover a substantial portion of the topsheet which may very likely reduce the absorbency properties of the diaper 1.

The topsheet attachment area(s) 14 may comprise one central topsheet attachment area 14a and two side topsheet attachment areas 14b, 14c on either side of the central topsheet attachment area 14a, as for example shown in FIGS. 1 to 8. This is particularly advantageous in order to ensure that the separator sheet 10 is correctly anchored to the topsheet 20 without increasing the stiffness of the diaper 1 to an extent that the diaper 1 becomes less comfortable for the wearer.

As mentioned hereinbefore, each of the first and second elastic cuffs 30a, 30b has a longitudinally extending distal edge 301a, 301b. The maximum transverse dimension $D_7$ of the one or more topsheet attachment area(s) 14 may be centered on the longitudinal centerline Y of the diaper 1 in flat state of the diaper 1 as for example shown in FIG. 1. Such a configuration helps to prevent in-use skewed separator sheet 10 which may cover the urination and/or the anus point or may inadvertently create gaps between the elastic cuffs 30a, 30b and the skin of the wearer, when the diaper 1 is applied to the wearer, gaps which may be responsible of leakage of bodily exudates in in-use conditions.

The maximum transverse dimension $D_7$ of the one or more topsheet attachment area(s) 14 may be comprised within the minimum transverse dimension $D_8$ between the longitudinally extending distal edges of the first and second elastic cuffs 301a, 301b, in flat state of the diaper 1 as for example shown in FIG. 1. The maximum transverse dimension $D_7$ of the one or more topsheet attachment area(s) 14 may be of 50% to 98% or 60% to 95% of the minimum transverse dimension $D_8$ between the longitudinally extending distal edges of the first and second elastic cuffs 301a, 301b, in flat state of the diaper 1. In such a configuration, the topsheet attachment area(s) 14 is/are therefore completely comprised between the first and second elastic cuffs 30a, 30b. This is particularly advantageous in order to reduce the risk that the distal edges of the elastic cuffs 301a, 301b may be inadvertently attached to the topsheet 20 when the separator sheet 10 is attached to the topsheet 20 during manufacturing of the diaper 1 which may be responsible for leakage of bodily exudates around the leg openings when the diaper 1 is applied to a wearer.

The topsheet attachment area(s) 14 may have any shape. They may have a rectangular shape as for example shown in FIGS. 1 to 8. Such rectangular shaped topsheet attachment areas 14 may be oriented parallel to the longitudinal centerline Y of the diaper 1, in flat state of the diaper 1. They may also have a round or an oval shape.

The attachment of the separator sheet 10 to topsheet 20 can be done by adhesive bonding, pressure bonding, ultrasonic bonding or any other attachment mean known in the art. The topsheet attachment area(s) 14 may comprise one or more individual bond(s). Such individual band(s) may be arranged according to a certain bonding pattern.

It should be understood that if a topsheet attachment area 14 comprises more than one individual bond with a shortest distance of less than 3 mm between them, these are herein considered as a single unitary topsheet attachment area.

The bonding pattern density of at least one of (or each of) the topsheet attachment area(s) 14 may be more than 20%, or more than 30%, or more than 40%, or more than 60%, up to 100%.

The topsheet 20 may be an apertured topsheet which comprise apertures to allow urine to pass to the absorbent core 22 under the topsheet 20.

In embodiments wherein the topsheet 20 is an apertured topsheet, each of the one or more topsheet attachment area(s) 14 may comprise one or more individual bond(s), wherein the at least one of (or each of) the topsheet attachment areas 14 have a bonding pattern density which is higher than the percentage open area of the topsheet 20 measured according to the topsheet effective aperture size and percentage open area measurement test method. In such embodiments, at least one of (or 50% more or each of) the individual bonds of at least one of (or each of) the topsheet attachment areas 14 may have a bigger size than at least one of (or 50% more or each of) the effective apertures of the topsheet 20. In such embodiments, the bonding pattern of at least one of (or each of) the topsheet attachment areas 14 may not overlap with the effective aperture pattern of the topsheet 20 if the individual bond (s) comprised by the topsheet attachment area(s) 14 have the same size or a smaller size than the effective apertures of the topsheet 20. These configurations are particularly advantageous in order to ensure a good anchorage of the separator sheet 10 to the topsheet 20.

The separator sheet 10 has a first side 101 and a second side 102. The first side 101 may be attached to both the elastic cuffs (30a, 30b) and the topsheet 20. Alternatively, the first side 101 may be attached to the elastic cuffs 30 and the second side 102 to the topsheet 20, as for example shown in FIGS. 1 to 5.

The topsheet attachment area(s) may be positioned closer to the front edge 1F of the diaper 1, or topsheet 20 or backsheet 21 than the cuff attachment areas 13a, 13b, as for example shown in FIGS. 1 to 5. This may reduce the risk that the separator sheet 10 creates a ramp which facilitates the migration of the feces to the front of the diaper 1.

Transverse Separator Sheet Material

The separator sheet 10 may be elastically extensible in at least the transverse direction, i.e. is able to extend upon application of a force, and to contract to about its original width upon release of said force, as described hereinafter. Only the top edge portion 16 of the separator sheet 10 may be elastically extensible in at least the transverse direction.

The separator sheet 10 may also be elastically extensible in the longitudinal direction.

The separator sheet 10 may be made of an elasticated sheet material 15, rendering the separator sheet 10 elastically extensible in the transverse direction at least. "Elasticated" when used herein for the separator sheet 10 or separator sheet material 15 (and also for the cuff or cuff web material) means that it is made of an inelastic sheet material that has been provided only in a specific area or in specific areas, i.e. the elasticated area(s), with an elastic material, e.g. one or more elastic bands or strands. The total surface area of the elasticated areas may for example be less than 50% of the total surface area of the separator sheet 10 or separator sheet material 15.

One or both of the top and bottom edge portions 16, 17 of the separator sheet 10 or separator sheet material 15 may be elasticated by application of one or more elastic band(s) or strand(s) extending substantially in transverse direction to a sheet material that may be inelastic e.g. an inelastic nonwoven sheet.

The separator sheet 10 may be elastically extensible in transverse direction at least. It may be elastically extensible in transverse direction at least over its surface area excluding the surface areas that are attached to the cuffs 30a, 30b and topsheet 20.

The separator sheet material 15 may be or may comprise an elastic film or a nonwoven sheet material or a laminate of an elastic film and a nonwoven sheet material. The nonwoven sheet material of the laminate can be positioned such that it is in contact with the skin of the wearer. Such a configuration of the laminate may provide more comfort to the wearer than when the elastic film is directly in contact with the skin of the wearer.

The nonwoven sheet material may be made of polyolefins known in the art, such as polyethylene and/or polypropylene, made into fibers, including bicomponent fibers that are then made into a nonwoven sheet. The nonwoven sheet material may be a necked nonwoven. The nonwoven sheet material may be a meltblown nonwoven or spunbond nonwoven or carded nonwoven; it may be a laminate thereof; for example it may be a laminate of spunbond or carded layer or layers and meltblown nonwoven layer(s).

The separator sheet material 15 may be or comprise a nonwoven sheet material that has a substantially uniform elastic behavior due to the application (e.g. substantially uniformly) of an elastic material to the nonwoven sheet material, in a way that it provides elasticity at least in transverse direction to the nonwoven sheet material; for example, elastic material may be sprayed or extruded onto a nonwoven sheet material, e.g. homogeneously or in a pattern such as stripes in transverse direction.

The separator sheet material 15 may be rectangular or square when laid out flat in relaxed, contracted state onto an even horizontal surface in relaxed, contracted state. The separator sheet material 15 may also be trapezoid when laid out flat in relaxed, contracted state onto an even horizontal surface in relaxed, contracted state, the top edge 11 and the bottom edge 12 of the separator sheet material 15 forming the two parallel sides of the trapezoid.

The separator sheet material 15 may be a barrier material; it may be hydrophobic; e.g. it may be hydrophilic and made hydrophobic with a hydrophobic surface coating, such as known in the art, for example a wax or a hydrophobic surface coating comprising one or more silicone polymers or fluorinated polymers.

The separator sheet 10 has an elastic behavior such that it can be significantly elastically extensible in transverse direction at least, during the process of making the diaper 1, and during application of the diaper 1 on the wearer, whilst providing in in-use conditions (during wear) correct alignment with the skin of the wearer, both when the wearer moves the legs apart and when the wearer moves the legs together. The separator sheet 10 should furthermore preferably have a certain tension in use to ensure it forms an effective separator (barrier) with a Z-direction dimension, to avoid migration of feces from the back to the front of the diaper 1. Furthermore, this tension should not be too high, otherwise the cuffs 30a, 30b, to which the separator sheet 10 is attached, are in use pulled too close together, leading to potential leakage issues of urine or feces outside or onto the cuffs 30a, 30b.

The separator sheet 10 may be elastically extensible in the transverse direction to a strain of at least 0.8, as measured according to the in-process two-cycle hysteresis test. The separator sheet 10 or separator sheet material 15 may be elastically extensible in the transverse direction to a strain of at least 1.2 or at least 1.5 or at least 2.0 or at least 2.5 or at least 3.0 or at least 3.5, as measured according to the in-process two-cycle hysteresis test. This can be done with any force suitable for processing elastic materials, typically a force of 20N or less, or typically a force of 10N or less. Therefore, the separator sheet 10 is such that it can be processed in a process that requires high extension, and that it contracts about immediately to about its original width, to allow high speed of processing.

It should be understood that the separator sheet 10 is considered as being elastically extensible in the transverse direction to a certain strain value if after having been extended to said strain value according to the in-process two-cycle hysteresis test, the percent set measured according to the in-process two-cycle hysteresis test is of 30% set or less or 20% or less or 10% or less. Having such a low set value ensures that the separator sheet material 15 is not damaged during processing of the diaper 1.

Cuffs

The diaper 1 has a pair of first and second longitudinally extending opposing elastic cuffs 30a, 30b, to which the separator sheet 10 (material 15) is attached.

Each of the cuffs 30a, 30b to which the separator sheet 10 is attached may be part of a unitary dual cuff sheet, comprising an outer cuff (leg cuff) and an inner cuff (barrier cuff), the latter being attached to the separator sheet 10.

Each cuff 30a, 30b has a longitudinally extending proximal edge that is joined to or attached to a diaper element, e.g. to the backsheet 21 or topsheet 20, or leg cuff, if present and an opposing, longitudinally extending, distal edge that is in use in contact with the skin of the wearer.

The cuffs 30a, 30b may be attached to the backsheet 21 adjacent and along the longitudinal sides of the backsheet 21 to have a cuff 30a, 30b on either side of the backsheet 21. The cuffs 30a, 30b may be attached to the topsheet 20, adjacent and along the longitudinal sides of the topsheet 20 to have a cuff 30a, 30b on either side of the topsheet 20.

The cuffs 30a, 30b may be mirror images of one another in the longitudinal centerline Y of the diaper 1, in flat state of the diaper 1. Each cuff 30a, 30b and/or its proximal edge may be curved or may be substantially straight.

The cuffs 30a, 30b may be made from a pair of cuff webs, comprising each multitude of cuffs which are then separated from one another to form individual cuffs.

The cuffs 30a, 30b are elastic or elasticated, for example as described above with respect to the separator sheet 10 or separator sheet material 15. The cuffs 30a, 30b may be at least, or only, elasticated along the distal edge thereof. Each cuff 30a, 30b may be a sheet material with one or more elastic strands attached thereto in stretched state. The one or more elastic strands may extend at least along the distal edge of the cuff 301a, 301b.

The proximal edge of each cuff 30a, 30b may be positioned along a longitudinal side of the absorbent core 22 or of the backsheet 21 or of the topsheet 20.

The proximal edge of each cuff 30a, 30b may be positioned longitudinally outwards of the absorbent core 22, so that the whole absorbent core 22 is in between the cuffs proximal edges.

The cuffs 30a, 30b may be attached such that in use they have Z-direction orientation.

Each of the cuffs' distal edges 301a, 301b may be further attached in the back edge 1B (e.g. waistband) and/or front (e.g. waistband) edge 1F of the diaper 1, or the topsheet 20 or backsheet 21 in respectively so-called front 35a, 35b and back 34a, 34b tack-down zones as for example shown in FIGS. 1 and 3.

The transverse distance between the front tackdown zone 35a of the first cuff 30a and the front tackdown zone 35b of the opposing second cuff 30b may equal the maximum transverse distance between the cuffs distal edges 301a, 301b in flat state of the diaper 1. This transverse distance may be at least 5.0 cm, or at least 6.0 cm, or at least 7.0 cm. This transverse distance may be up to the average transverse dimension of the diaper 1 measured in the crotch region of the diaper 1, in flat state of the diaper 1. The same may apply to the transverse distance between the back tackdown zone 34a of the first cuff 30a and the back tackdown zone 34b of the opposing second cuff 30b.

Each cuff 30a, 30b may have an elastic tension of at least 20 grams (0.2N) and up to 100 grams (1.0N), or up to 50 grams (0.5N), when extended to a 95% or 80% extension strain.

The cuffs 30a, 30b or cuff web material may comprise a nonwoven sheet material. The same nonwoven sheet materials as the ones used to make the transverse separator sheet 10 may be used. The nonwoven sheet material may be a nonwoven barrier sheet material that is liquid impermeable, as known in the art, including for example nonwoven laminate(s) with one or more spunbond layers and/or carded layers, and one or more meltblown layers. The fibers used to form the nonwoven sheet material may be selected from polypropylene fibers, polyethylene fibers, bicomponent fibers, nanofibers and any combinations thereof.

The cuffs 30a, 30b or part thereof, and/or the separator sheet 10 or part thereof may comprise a skin care composition, e.g. lotion, as known in the art.

The separator sheet 10 or separator sheet material 15 may be attached to the cuffs 30a, 30b in relaxed, contracted state. The cuffs 30a, 30b may then be spread apart, thereby stretching the separator sheet 10 or separator sheet material 15.

The cuffs 30a, 30b may have any suitable dimensions, for example depending on the diaper-dimensions. They may extend about the full length of the diaper 1. They may have a transverse dimension perpendicular to longitudinal centerline Y of the diaper 1 of for example at least 30 mm, or for example at least 40 mm.

Topsheet

The diaper 1 comprises a topsheet 20. The topsheet of the diaper 1 herein may be made of any suitable material known in the art, provided it allows urine to pass. Hereto, it may be made of a urine permeable material, including hydrophilic material, or material treated to be hydrophilic. As explained hereinbefore, the topsheet 20 may be an apertured topsheet which comprise apertures to allow urine to pass to the absorbent core 22 under the topsheet 20. The topsheet 20 may comprise apertures with an effective aperture size of at least 0.2 square millimeters or at least 0.3 square millimeters as measured according to the topsheet effective aperture size and percentage open area measurement test method.

The topsheet may be either hydrophilic or hydrophobic.

The separator sheet 10 or separator sheet material 15 may be attached to the cuffs 30a, 30b and to the topsheet 20 in relaxed, contracted state. The cuffs 30a, 30b may then be spread apart, thereby stretching the separator sheet 10 or separator sheet material 15; the cuffs 30a, 30b may for example be attached to the topsheet 20 prior to spreading or subsequent to the spreading step.

The topsheet 20 may be a stretchable material, or a material that is extensible, for example by the provision of folds. The topsheet 20 may for example comprise one or more longitudinally extending Z-fold(s) prior to attachments to the separator sheet 10 (or separator sheet material 15) and/or to the cuffs 30a, 30b. Once the topsheet 20 is unfolded, it no longer has the folds, e.g. fold(s), but it may still have the longitudinally extending fold lines.

Preferred topsheet materials are nonwoven materials, including laminates and/or materials with apertures, such as apertured films, aperture formed films.

The topsheet 20, or for example only the crotch and/or back region thereof, may comprise a skin care composition, e.g. a lotion.

Other Elements of the Diaper

The diaper 1 has also at least a backsheet 21 and an absorbent core 22, the absorbent core 22 comprising for example multiple layers, including for example one or more acquisition layers, in liquid communication with the topsheet 20, and a storage layer, comprising superabsorbent polymer material/particles at least, typically enclosed by a core cover material.

The acquisition layer or layers may comprise any acquisition material which is capable of acquiring urine or runny feces, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges.

The storage layer may comprise any of the above material, but it typically at least comprises superabsorbent polymeric material/particles; for example; the absorbent storage layer may comprise more than 80% by weight (e.g. excluding core wrap) of superabsorbent polymeric (particulate) material; it may be free of cellulose (airfelt) material.

The backsheet 21 may be liquid impervious, as known in the art. The liquid impervious backsheet 21 preferably comprises a thin plastic film such as a thermoplastic film, for example having a thickness of about 0.01 mm to about 0.05 mm. Suitable backsheet materials comprise typically breathable material, which permit vapors to escape from the diaper 1 while still preventing exudates from passing through the backsheet 21. Suitable backsheet films include those manufactured by Tredegar Industries Inc. of Terre Haute, Ind. and sold under the trade names X15306, X10962 and X10964.

The backsheet 21, or any portion thereof, may be elastically extendable in one or more directions. The backsheet 21 may be attached or joined to a topsheet 20, the absorbent core 22, or any other element of the diaper 1 by any attachment means known in the art. It may be highly preferred that the longitudinal side edges of the topsheet 20 and backsheet 21 are directly attached to one another.

The diaper 1 may also include a sub-layer disposed between the topsheet 20 and the absorbent core 22, capable of accepting, and/or immobilizing bodily exudates, typically fecal material.

The diaper 1 herein may have a fastening system, typically joined to the waistband, as known in the art. Preferred fastening systems comprise fastening tabs and landing zones, wherein the fastening tabs are attached or joined to the back region of the diaper 1 and the landing zones are part of the front region A of the diaper 1.

The diaper 1 may be a pant-type diaper that has fastened side portions.

Test Methods

Projected Bond Measurement Test Method:

This method determines the projected bond length of a cuff attachment area. The diaper 1 is laid out flat onto an even horizontal surface. A first longitudinally extending line $L_1$ parallel to the longitudinal centerline Y of the diaper 1 and in contact with the point of the cuff attachment area 13 which is the closest to the longitudinal centerline Y of the diaper 1 is drawn, as for example shown in FIGS. 6, 7 and 8. A second longitudinally extending $L_2$ parallel to the first longitudinally extending line $L_1$ is drawn further away from the longitudinal centerline Y with a distance $D_3$ between the first and the second longitudinally extending lines $L_1$, $L_2$ of 5 mm, as for example shown in FIGS. 6, 7 and 8. A first laterally extending line $L_3$ perpendicular to the longitudinal centerline Y of the diaper 1 and in contact with the point of the cuff attachment area 13 which is the closest to the front edge 1F of the diaper 1 and laterally comprised between the first and the second longitudinally extending lines $L_1$, $L_2$ is drawn, as for example shown in FIGS. 6, 7 and 8. A second laterally extending line $L_4$ perpendicular to the longitudinal centerline Y of the diaper 1 and in contact with the point of the cuff attachment area 13 which is the closest to the back edge 1B of the diaper 1 and laterally comprised between the first and the second longitudinally extending lines $L_1$, $L_2$ is drawn as for example shown in FIGS. 6, 7 and 8.

The distance $D_4$ between the first and second laterally extending lines $L_3$, $L_4$ corresponds to the projected bond length of the cuff attachment area 13.

In-Process Two Cycle Hysteresis Tests:

Equipment and Preparation of Samples:

Suitable instruments for this test include tensile testers commercially available from MTS Systems Corp., Eden Prairie, Minn. (e.g. Alliance RT/1 or Sintech 1/S) or from Instron Engineering Corp., Canton, Mass. or from Zwick/Roell, Kennesaw, Ga./Ulm, Germany.

The tester is equipped with a grip face set in the upper and lower grips, where each set has one rubber-coated face (80 A shore hardness) and one contact line face (metal), with a screw mechanism that engages the contact line face into the rubber-coated face to prevent slippage. The length of the upper and lower grips is at least as long as the clamped length of the specimen to be tested, the grip length being the dimension of the grip parallel to the length of the specimen. A load cell is used so that the maximum load measured is within 10-90% of the maximum capacity of the load cell. The instrument is calibrated according to the manufacturer's specification.

Before obtaining the specimen from the diaper, the diaper is kept in a relaxed state at ambient temperature (22° C.+/− 5° C.) for at least 24 hours.

The separator sheet 10 is cut to obtain a rectangular specimen having a transverse dimension (width) of 20 mm centered on the longitudinal centerline Y of the diaper 1 and a longitudinal dimension (length) of 30 mm, both transverse and longitudinal dimensions being measured in relaxed, contracted state when the specimen is laid out flat onto an even horizontal surface. The transverse dimension and longitudinal dimension of the specimen are measured parallel to respectively the transverse dimension and longitudinal dimension of the separator sheet 10. The transversely extending edge of the specimen which is the closest to the top edge 11 of the separator sheet 10 is referred hereinafter as the top edge of the specimen. The opposite transversely extending edge of the specimen is referred hereinafter as the bottom edge of the specimen.

For separator sheet(s) 10 that has/have a minimum length in relaxed, contracted state between the top edge and the bottom edge of more than 30 mm, the specimen is cut such that it does include the top edge of the separator sheet 10.

Clamped Length

The clamped length is the length of specimen in relaxed, contracted state which is clamped between the grips starting from the top edge of the specimen. The clamped length is equal to the average of the first and second projected bond lengths $D4_a$, $D4_b$. The first and second projected bond lengths $D4_a$, $D4_b$, are measured according to the projected bond measurement test method prior to cutting of the test specimen.

Before starting the test (details below), each specimen and the equipment must equilibrate at 22° C. (+/− 1° C.), for at least 1 hour, for the in-process two cycle hysteresis tests herein.

The force reading on the instrument is zeroed to account for the mass of the fixtures and grips. The specimen is mounted into the grips with no slack and the force measured is between 0.00 N and 0.01 N. The data acquisition frequency is 100 Hz; the force, time and engineering strain data are acquired during all segments of the hysteresis tests.

The specimen is mounted with 10 mm of its width in relaxed, contracted state between the lines of contact of the grips (gauge width) and 5 mm of its width outside the line of contact of each grip. The clamped length of the specimen is clamped in the grips. The remaining length of the specimen (which equals the length of the specimen minus the clamped length) is excluded from the grips. The clamped length is specified above.

In the following, engineering strain is defined as $\Delta W/W_0$ with $\Delta W = W_t - W_0$, wherein $W_0$ is the initial sample width and $W_t$ is the sample width at time t.

In-Process Two-Cycle Hysteresis Test (Measurement at 22° C.):

The In-Process two-cycle hysteresis test is performed as follows:

1. Slack Adjustment:

Move the crosshead at a speed of 13 mm/minute until the slack adjustment preload force of 0.02 N is achieved. The distance between the lines of contact of the grips at the slack adjustment preload force of 0.02N is the adjusted gauge width $W_{GAdj}$ which is equal to the initial sample width $W_0$ (engineering strain=0%).

2. First Cycle:

The specimen is extended to the tested engineering strain at a crosshead speed of 800 mm/min. There is no hold at this engineering strain. The crosshead is then returned to the adjusted gauge width $W_{GAdj}$, at a crosshead speed of 800 mm/min, and held at this engineering strain for 60 seconds.

3. Second Cycle:

The specimen is extended to the same engineering strain as the engineering strain in the first cycle, at a crosshead speed of 800 mm/min. There is no hold at this engineering strain. The crosshead is then returned to the adjusted gauge width $W_{GAdj}$ at a crosshead speed of 800 mm/min and held at this engineering strain for 60 seconds.

Each specimen of separator sheet of the diaper is inspected for damage after the In-Process two-cycle hysteresis test. Separator sheet material of the invention must have no damage after the test. The damage is defined via the percent set. The percent set (% Set) is defined as the engineering strain, in percent, where the $2^{nd}$ cycle extension force of 0.069 N (7 gram-force) is measured. If the percent set is lower than 30%, the specimen is considered as not being damaged and is therefore considered as being elastically extensible to tested engineering strain.

A minimum of 5 specimens are measured, to determine the average test values, average data being provided by the tensile tester test software (e.g. Alliance RT1 MTS Instrument is TestWorks4 version 4.08 B)

The method report specifies the used engineering strain, the specimen dimensions and the clamped length used for the measurements.

The property of the separator sheet reported for the method is the % set.

Topsheet Effective Aperture Size and Percentage Open Area Measurement Test Method:

The effective aperture size and percentage open area are determined by the following procedure using the image analysis system described below. The procedure has three principal steps: image acquisition, i.e., obtaining representative images of areas on the surface of the topsheet; image measurement, i.e., measuring the percentage open area of an image and of individual apertures and their perimeters; and data analysis, i.e., exporting the percentage open area, individual aperture area, and perimeter measurements to a spreadsheet where frequency distributions, sum of area distributions, and hydraulic radius computations are made.

An image analysis system having a frame grabber board, microscope, camera and image analysis software is utilized. A model DT2855 frame grabber board available from Data Translation of Marlboro, Mass. is provided. A VH5900 monitor microscope, a video camera, having a VH50 lens with a contact type illumination head available from the Keyence Company of Fair Lawn, N.J. are also provided and used to acquire an image to be saved to computer file. The Keyence microscope acquires the image and the frame grabber board converts the analog signal of this image into computer readable digital format. The image is saved to computer file and measured using suitable software such as the Optimas Image Analysis software, version 3.1, available from the BioScan Company of Edmonds, Wash. In order to use the Optimas Image Analysis software, the computer should have Windows software, version 3.0 or later, available from the Microsoft Corporation of Redmond, Wash. and also have a CPU at least equivalent to the Intel 80386. Any suitable desk top PC may be used, with a 486 DX33 type PC having been found to be particularly suitable. Images being saved to and recalled from file were displayed on a Sony Trinitron monitor model PVM-1343MO with a final display magnification of about 50×.

The image acquisition step, noted above requires 10 different regions from a representative topsheet sample of a particular type of diaper or from sample material to be tested. Each region is rectangular, measuring about 5.8 millimeters by 4.2 millimeters. The sample is placed on a black mat board to increase the contrast between the apertures and the portion of the sample that defines the apertures. The mean gray level and standard deviation of the black mat board were 16 and 4, respectively.

Images are acquired with room lights off using the Keyence monitor microscope mounted on a copystand directly above the sample. The Keyence light source illuminating the sample is adjusted and monitored with the Optimas software to measure the mean gray level and standard deviation of a 0.3 density wedge on a Kodak Gray Scale available from Eastman Kodak Company of Rochester, N.Y. The control of Keyence light source is adjusted so that the mean gray level of the illuminated wedge is 111±1 and the standard deviation is 10±1. All images were acquired during a single time period, and the Keyence light source is monitored by measuring the mean gray level and standard deviation of the wedge throughout the image acquisition process.

In measuring an individual aperture, only the effective aperture size is of interest. Measuring the effective aperture size quantifies the aperture size intended to contribute to the porosity of the topsheet, and account for contributions fibers and fiber bundles that traverse an area intended to be an aperture. An effective aperture is any hole through the topsheet having a gray level less than or equal to 18 using image acquisition parameters as described herein. Thus, an intended aperture may be divided into plural effective apertures by traverse fibers.

The image analysis software is calibrated millimeters by a ruler image acquired from the sample images. A 3 by 3 pixel averaging filter found in the Optimas 3.1 Image menu is applied to each saved image to reduce noise. The apertures are detected in the gray level range of 0 through 18. An aperture that is not fully contained within the 5.8 by 4.2 viewing area is not considered in the individual area and perimeter measurements. Therefore, area and perimeter averages and distributions are not affected by apertures that are not wholly contained within the field of view.

However, individual apertures that could not be fully viewed in the image are included in the percentage open area calculation. This difference occurs because the percent open area is simply the image of pixel ratios from 0 through 18 to the total number of pixels in the image. Areas having a gray level 19 or greater were not counted in the open area calculation.

The percentage open area for the average of 10 images for each topsheet is measured using the Optimas Image Analysis software. The percentage open area is defined as the ratio of the number of pixels having a gray level from 0 through 18 to the total number of pixels for the image. The percentage open area is measured for each image representing one particular region from a topsheet sample. The percentage open area from each of the 10 individual images is then averaged to yield a percentage open area for the entire sample.

The data analysis is conducted by an Excel spreadsheet, also available from the Microsoft Corporation of Redmond, Wash. The Excel spreadsheet organized the percentage open area, aperture area, and aperture perimeter measurements obtained from the Optimas software. Sample averages and standard deviations, size and frequency distributions of individual aperture areas and hydraulic radius computations (area divided by perimeter) for individual apertures are obtained using the spreadsheet.

Distributions of individual aperture area are also computed using the Excel spreadsheet. The apertures are sorted into bins of certain size ranges. The number of aperture areas falling into certain size ranges of interest is determined as well as the sum of the areas within each range. The ranges are set in increments of 0.05 square millimeters. These areas are expressed as a percentage of the total open area of the sample. The frequency and sum of the area distributions are obtained by combining individual aperture measurements from all 10 images for each sample.

EXAMPLES

Four different diapers comprising a transverse separator sheet are prepared. Each of the four diapers is a Pampers Active Fit™ size 4 diaper commercially available in Germany in June 2012 to which a transverse separator sheet is attached. Each of the four diapers comprises a first and a second cuff attachment area wherein the top edge portion of the separator sheet is attached by pressure bonding to the crotch region of the elastic cuffs of the diaper. Each of the four diapers also comprise one central topsheet attachment area and two side topsheet attachment areas wherein the bottom edge portion of the separator sheet is attached by pressure bonding to the topsheet of the diaper. Each of the four diaper has a longitudinal dimension of 488 mm.

The first and second cuff attachment areas have a rectangular shape with a longitudinal dimension of 15 mm and a lateral dimension of 13 mm and are the inner edge of each of the first and second cuff attachment areas is oriented parallel to the longitudinal centerline Y of the diaper and are mirror images of one another in the longitudinal centerline Y of the diaper, in flat state of the diaper. The central and the two side topsheet attachment areas have a rectangular shape oriented parallel to the lateral centerline X of the diaper. Each of the central and the two side topsheet attachment areas has a longitudinal dimension of 6 mm and a lateral dimension of 20 mm and are spaced with a lateral dimension between two adjacent topsheet attachment areas of 7.5 mm.

Each of the four diapers is made of a different separator sheet material as described hereinafter. Each of the separator sheet material is rectangular and has a longitudinal dimension of 85 mm and a transverse dimension of 100 mm when laid out flat onto an even horizontal surface in relaxed, contracted state and is oriented such that the separator sheet material is extensible in the transverse direction.

Examples 1 to 3

The transverse separator sheets of the diapers of examples 1, 2 and 3 are made of the activated trilaminate separator sheet materials shown in Table 1.

The activated trilaminate separator sheet materials, shown in Table 1, are made by adhesive lamination of an extrusion bilaminate (EBL, NW1/A1/B1/A2) to a second nonwoven (NW2), followed by activation to release the stretch.

EBL useful in the present invention are disclosed in U.S. Pat. No. 8,168,853, by Autran, etc., and are made by Clopay Plastic Product of Mason, Ohio. The EBL is made by bringing one nonwoven (NW1) onto a freshly extruded and drawn-down multilayer film (A1/B1/A2) in close contact to each other at the nip of two compression rolls under controlled temperature and pressure conditions to form a bond between the tie layer (A1) of the extruded multilayer film (A1/B1/A2) and the fibers of the nonwoven (NW1).

The EBL comprises a first nonwoven (NW1) and a 15 gsm multilayer film comprising a tie layer (A1), an inner layer (B1), and a skin layer (A2). The composition of the film inner layer (B1) for examples 1 and 2 is a weight % blend of 92% Vistamaxx 6102, 1% Ampacet 10562 (process aid) and 7% Ampacet 110361 (white masterbatch with 70% $TiO_2$). The composition of the film inner layer (B1) of the EBL of example 3 is a weight % blend of 87% Vistamaxx 6102, 5% Inspire Dow 118 PP, 1% Ampacet 10562 and 7% Ampacet 110361. The composition of A1 is compositionally identical to A2 and is a weight % blend of 24% Infuse 9107, 75% Elite 5800, and 1% Ampacet 10562.

The first nonwoven (NW1) used in the EBL of examples 1, 2 and 3 is a 15 gsm spunbond bicomponent PP/PE (50/50, core/sheath) nonwoven from Pegas Nonwovens (Czech Republic). The second nonwoven (NW2) adhesively laminated to the EBL of examples 1 and 2 is a 20 gsm spunbond bicomponent PP/PE (70/30, core/sheath) nonwoven from Fiberweb (Washougal, Wash.), while in example 3, the second nonwoven (NW2) is made of the same nonwoven as the first nonwoven (NW1), i.e. a 15 gsm spunbond bicomponent PP/PE (50/50, core/sheath) nonwoven from Pegas Nonwovens (Czech Republic). Vistamaxx 6102 resin is available from ExxonMobil Chemical Company of Houston, Tex. Ampacet 10562 and 110361 are available from Ampacet Corporation of Cincinnati, Ohio. Elite 5800 PE and Infuse 9107 resins are available from The Dow Chemical Company of Midland, Mich.

For examples 1, 2 and 3, the aged roll of EBL is combined with the second nonwoven (NW2) using a high speed adhesive lamination process, with the addition of approximately 4.5 gsm of Bostik H2861 adhesive (commercially available from Bostik Inc. of Wauwatosa, Wis.) to the A2-NW2 interface to form a trilaminate. For examples 1 and 3, the lamination is followed by mechanical activation by a ring rolling activation process. For example 2, the lamination is followed by mechanical activation by High Speed Research Press (HSRP) activation. Lamination and activation details are shown in Table 1.

HSRP activation process is described in U.S. Pat. Nos. 7,062,983 and 6,843,134. HSRP activation process refers to the use of aluminum plates with inter-meshing teeth to selectively stretch portions of the trilaminate such that the nonwoven layers are broken and/or elongated and the elastic multilayer film is able to extend and retract without being unduly encumbered by the nonwoven layers. The activation plates used for the HSRP activation have inter-meshing teeth with a tip radius of 0.1 mm, a root radius of 0.5 mm and tooth height of 10.15 mm.

TABLE 1

Examples of activated trilaminate separator sheet materials

| | Examples | | |
|---|---|---|---|
| | 1 | 2 | 3 |
| Trilaminate Structure = adhesive free bilaminate NW1/A1/B1/A2 + 4.5 gsm H2861 adhesive + NW2 | | | |
| NW1 | 1[1] | 1 | 1 |
| A1 = A2 | Infuse/PE blend[3] | Infuse/PE blend | Infuse/PE blend |
| B1 | VM blend-1[4] | VM blend-1[4] | VM blend-2[5] |
| NW2 | 2[2] | 2 | 1 |
| total film basis weight | 15 gsm | 15 gsm | 15 gsm |
| multilayer film structure | A1/B1/A2 | A1/B1/A2 | A1/B1/A2 |
| Details of adhesive lamination (combining bilaminate + NW) and activation | | | |
| Interface with Adhesive | A2-NW2 | A2-NW2 | A2-NW2 |
| Adhesive type (Bostik) | H2861 | H2861 | H2861 |
| Adhesive basis weight (gsm) | 4.5 gsm | 4.5 gsm | 4.5 gsm |
| Nip Gap | 0.005" | 0.005" | 0.005" |
| lamination line speed (m/sec) | 5.4 | 5.4 | 6.1 |
| activation type | on line @ 5.4 m/sec | HSRP @ 0.3 m/sec with 250 millisecond dwell time | on line @ 6.1 m/sec |

TABLE 1-continued

Examples of activated trilaminate separator sheet materials

| | Examples | | |
|---|---|---|---|
| | 1 | 2 | 3 |
| activation pitch, inches (mm) | 0.100" (2.54 mm) | 0.098" (2.49 mm) | 0.100" (2.54 mm) |
| Depth of engagement, DOE, inches (mm) | 0.160" (4.06 mm) | 0.220" (5.59 mm) | 0.200" (5.08 mm) |
| Average Strain of activation (%) | 240% | 364% | 318% |

[1]NW = 1 = 15 gsm (50/50 core/sheath, PP/PE) bicomponent spunbond, produced at Pegas Nonwovens (Czech Republic).
[2]NW = 2 = 20 gsm (70/30 core/sheath, PP/PE) bicomponent spunbond, produced at Fiberweb (Washougal, Washington).
[3]Infuse/PE blend = Infuse 9107 (24%), Elite 5800 PE (75%), Ampacet 10562 (1%) in weight %.
[4]VM blend-1 = Vistamaxx 6102 (92%), Ampacet 10562 (1%), Ampacet 110361 (7%) in weight %.
[5]VM blend-2 = Vistamaxx 6102 (87%), Dow 118 PP (5%), Ampacet 10562 (1%), Ampacet 110361 (7%) in weight %.

Example 4

The transverse separator sheet of the diapers of example 4 is made of the back ear material of Pampers Active Fit™ diapers commercially available in Germany in June 2012.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it atone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An infant or adult diaper having a longitudinal centerline and a lateral centerline perpendicular to the longitudinal centerline, wherein the diaper comprises a topsheet and a backsheet and positioned therein between an absorbent core, first and second longitudinally extending opposing elastic cuffs on either longitudinal side of the topsheet, the diaper having a crotch region, positioned in between a front region and a back region, wherein the diaper comprises a transverse separator sheet made of a separator sheet material, the transverse separator sheet having a transversely extending top edge and top edge portion and an opposing transversely extending bottom edge and a bottom edge portion, wherein
    parts of the top edge portion are attached to the cuffs in the crotch region or front region to form a first cuff attachment area and a second opposing cuff attachment area, each cuff attachment area having an inner edge towards the longitudinal centerline of the diaper; and
    the bottom edge portion is attached to the topsheet at one or more topsheet attachment areas, and wherein the first cuff attachment area has a first projected bond length as measured according to the projected bond measurement test method and the second cuff attachment area has a second projected bond length as measured according to the projected bond measurement test method wherein the average of the first and second projected bond lengths is from 1% to 20% of the longitudinal dimension of the crotch region of the diaper, in a flat state of the diaper.

2. The diaper according to claim 1, wherein each of the first and second elastic cuffs has a longitudinally extending distal edge, and a minimum transverse dimension between either of the longitudinally extending distal edges of a cuff and an inner edge of the a cuff attachment area thereon is 0 to 15 mm.

3. The diaper according to claim 1, wherein the first and second cuff attachment areas are mirror images of one another about the longitudinal centerline of the diaper, in flat state of the diaper.

4. The diaper according to claim 1, wherein the inner edge of either of first and second cuff attachment areas forms an angle $\alpha$ of more than 0° with the longitudinal centerline of the diaper, in the flat state of the diaper.

5. The diaper according to claim 1, wherein the first and second cuff attachment areas have a rectangular shape.

6. The diaper according to claim 1, wherein each of the one or more topsheet attachment areas has a maximum longitudinal dimension of from 1% to 10% of the longitudinal dimension of the crotch region of the diaper.

7. The diaper according to claim 1, wherein a bonding pattern density of at least one of the topsheet attachment area(s) is more than 20%.

8. The diaper according to claim 1, wherein the topsheet is an apertured topsheet, wherein each of the one or more topsheet attachment areas comprises one or more individual bonds, wherein:
    a. at least one of the topsheet attachment areas has a bonding pattern density which is higher than the percentage open area of the topsheet measured according to the topsheet effective aperture size and percentage open area measurement test method; or
    b. at least one individual bond in at least one of the topsheet attachment areas has a bigger size than at least one of the effective apertures of the topsheet; or
    c. the bonding pattern of at least one of the topsheet attachment areas does not overlap with the effective aperture pattern of the topsheet.

9. The diaper according to claim 1, wherein the one or more topsheet attachment areas comprise one central topsheet attachment area and two side topsheet attachment areas on either side of the central topsheet attachment area.

10. The diaper according to claim 1, wherein the maximum transverse dimension of the one or more topsheet attachment areas is centered about the longitudinal centerline of the diaper, in flat state of the diaper.

11. The diaper according to claim 1, wherein each of the first and second elastic cuffs has a longitudinally extending distal edge and a maximum transverse dimension of the one or more topsheet attachment areas is disposed within the minimum transverse dimension between the longitudinally extending distal edges of the first and second elastic cuffs, in flat state of the diaper.

12. The diaper according to claim 11, wherein the maximum transverse dimension of the one or more topsheet attachment areas is 50% to 98% of the minimum transverse dimension between the longitudinally extending distal edges of the first and second elastic cuffs, in flat state of the diaper.

13. The diaper according to claim 1, wherein the transverse separator sheet is elastically extensible in the transverse direction to a strain of at least 0.8, as measured according to the in-process two-cycle hysteresis test.

14. The diaper according to claim 1, wherein the separator sheet material comprises an elastic film, a nonwoven sheet material, a laminate of an elastic film and a nonwoven sheet material, or comprises one or more elastic bands or strands.

* * * * *